United States Patent [19]

Danforth

[11] 4,272,878
[45] Jun. 16, 1981

[54] METHOD FOR MAKING HYPEREXTENSION ORTHOSIS

[76] Inventor: Michael B. Danforth, 718 Highland St., Altamonte Springs, Fla. 32701

[21] Appl. No.: 903,498

[22] Filed: May 8, 1978

[51] Int. Cl.² ............. B29C 13/00; B29C 25/00; B29D 31/00
[52] U.S. Cl. ................. 29/526 R; 264/138; 264/222; 264/227; 264/257
[58] Field of Search ............. 264/222, 257, 258, 225, 264/138, 227; 128/68, 68.1, 69, 77, 78, 87, 89, 90, 91; 29/526 R

[56] References Cited

U.S. PATENT DOCUMENTS

| | | | |
|---|---|---|---|
| 224,784 | 2/1880 | Johnstone | 264/222 |
| 3,095,875 | 7/1963 | Davidson et al. | 128/78 |
| 3,274,996 | 9/1966 | Jewett | 128/78 |
| 3,680,548 | 8/1972 | Brown | 128/69 |
| 3,771,513 | 11/1973 | Velasquez | 128/78 |
| 3,871,367 | 3/1975 | Miller | 264/222 |

OTHER PUBLICATIONS

Anon., "Appliances For Spine and Trunk," Orthopedic Appliance Atlas (1952) p. 239.

*Primary Examiner*—W. E. Hoag

[57] ABSTRACT

An anterior total contact hyperextension orthosis apparatus method of making a hyperextension orthosis. A stockinette is placed on a patient's body and marked for pre-determined patient features. A cast is formed on the patient's body for making a drape mold. The stockinette markings transfer to the cast and to the mold. The mold is modified including conforming the mold to the measured patient's breast portion and breast position, and the orthosis body is drape formed on the mold. The orthosis body is a molded plastic material having a breast support portion formed to be supported on the patient's breast, along with a pubic support portion and a center support portion formed between the breast support portion and the pubic support portion to conform to the patient's body therebetween to apply pressure primarily to soft tissue. Straps are attached to the anterior body portion and to a lumber pad for attaching the brace to the patient.

5 Claims, 11 Drawing Figures

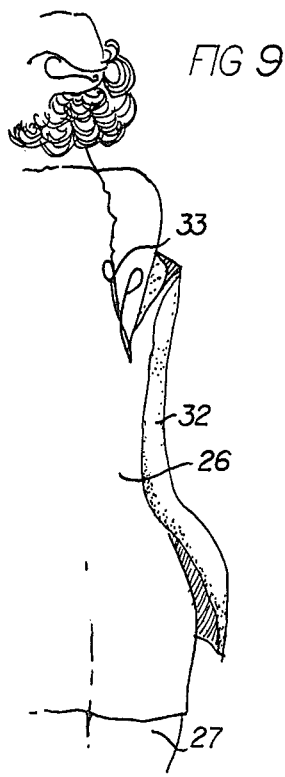
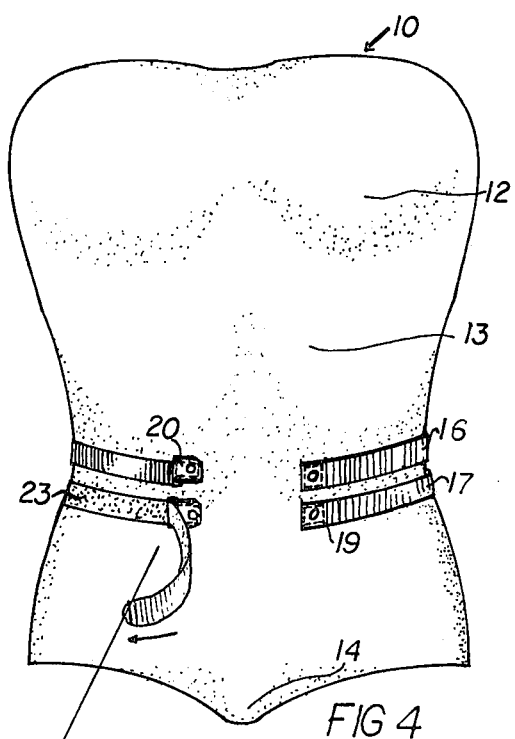
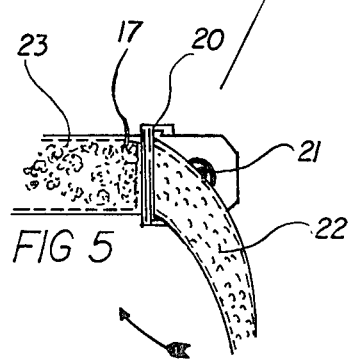
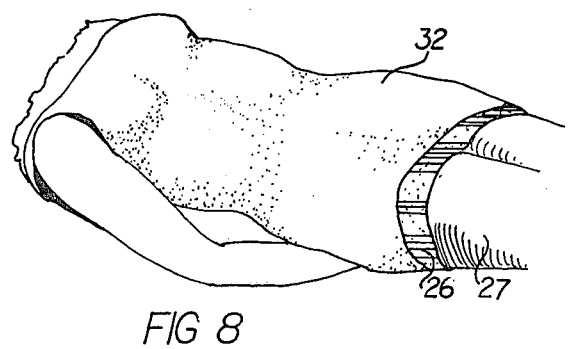

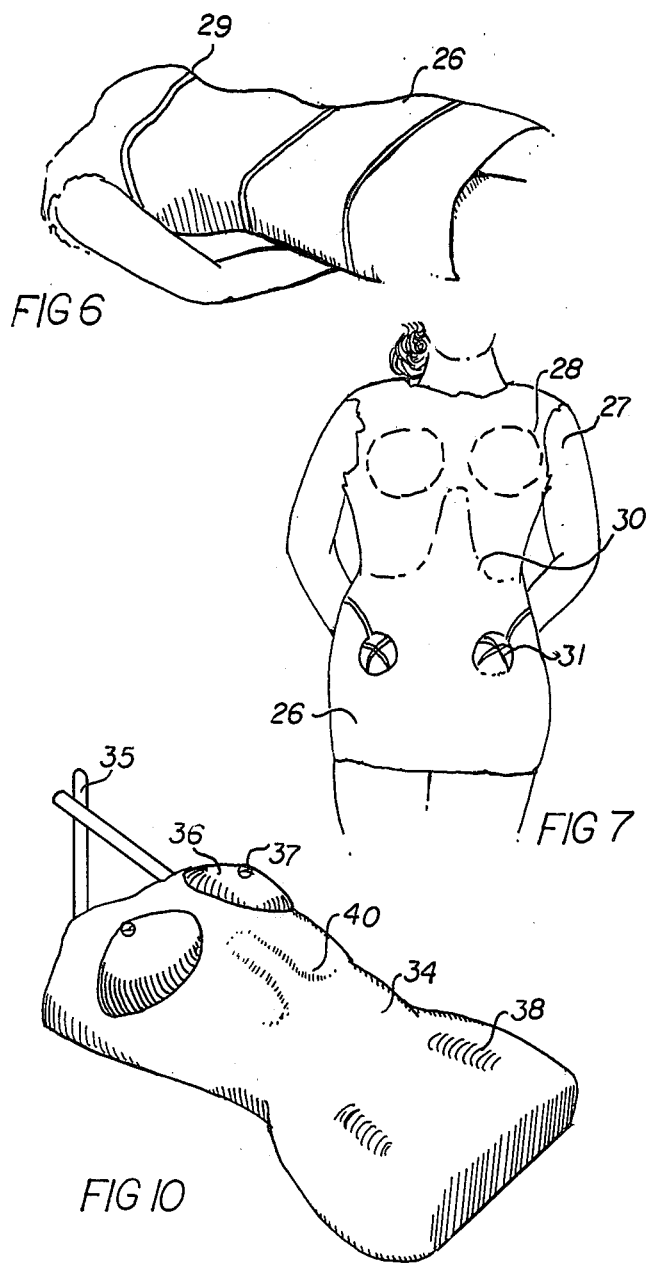
FIG 6
FIG 7
FIG 10
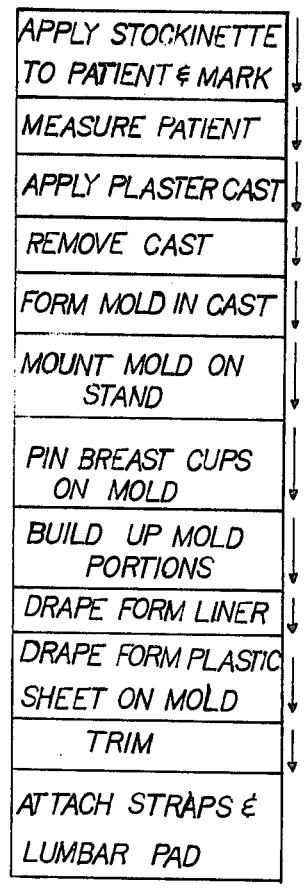
| APPLY STOCKINETTE TO PATIENT & MARK |
| MEASURE PATIENT |
| APPLY PLASTER CAST |
| REMOVE CAST |
| FORM MOLD IN CAST |
| MOUNT MOLD ON STAND |
| PIN BREAST CUPS ON MOLD |
| BUILD UP MOLD PORTIONS |
| DRAPE FORM LINER |
| DRAPE FORM PLASTIC SHEET ON MOLD |
| TRIM |
| ATTACH STRAPS & LUMBAR PAD |
FIG 11

METHOD FOR MAKING HYPEREXTENSION ORTHOSIS

BACKGROUND OF THE INVENTION

The present invention relates to orthosis devices and especially to a total contact hyperextension orthosis and a method of making the same.

Surgical braces of the present type have been commonly used in the past, which include the Jewett hyperextension back brace having a rigid three-point hyperextension system, including a sternal plate for pressing against the patient's sternum, which has a sternal pad and sternal bars connecting the sternal plate to side pads which are in turn connected to the lumbar pads and which has pubic bars attached to the side pads and to a pubic pad which is contoured to fit over the groin of the patient. A brace of this type can be seen in U.S. Pat. No. 3,274,996. Other braces may be seen in U.S. Pat. No. 3,351,053 and in U.S. Pat. No. 3,871,367. This latter patent has a pelvic brace formed like a girdle with an outer layer of hard, substantially rigid plastic material and an inner layer of soft compressible plastic material bonded to the outer layer, with the girdle being shaped to engage the person's pelvis, and being split vertically along the anterior and posterior vertical portions, and has specially curved sections to engage the iliac crest of the wearer, which portion has appreciably thicker compressible inner layers thereon. This patent also has a method of making such a brace. U.S. Pat. No. 3,680,548 shows a method of making an orthopedic correctional cast. In U.S. Pat. No. 224,784, a stiffening jacket or envelope for supporting parts of the human body is provided.

The present invention deals with a brace of the type taught in the Jewett U.S. Pat. No. 3,274,996, but which provides the principal support against soft tissue, including the patient's breast, rather than against the sternum, thereby relieving the uncomfortable pressure against the patient's bones. To accomplish this, however, the brace must be made to conform to an individual patient's body and breasts in a manner to place a uniform support over the body. The molding of a custom brace, however, leaves the breast positioned improperly for such support, and this must be measured, marked and corrected in the forming of the present orthosis. In addition, the present orthosis provides a total contact anterior support for the anterior portion thereof.

SUMMARY OF THE INVENTION

A method of making an anterior total contact hyperextension orthosis includes the steps of marking a stockinette on a patient for pre-determined positioning, and forming a cast on a patient's body, then removing the cast and forming a drape mold therein. The marks on the stockinette are transferred to the cast and to the mold. The mold is mounted on a stand and is then modified at the marked areas, including attaching molded parts to conform to the measured size and position of the patient's breast portions. The lining and the anterior hyperextension orthosis body is drape formed on the mold, and flexible straps are attached thereto, along with a lumbar pad, and the orthosis may be attached to the patient with velcro connections on the straps. The anterior total contact hyperextension orthosis includes the orthosis body drape molded to conform to the patient's body, and having a breast support portion formed to be supported on the patient's breast, along with a pubic support portion and a center support portion formed between the breast and pubic support portions, and also having side support pads. The orthosis body conforms to the patient's anterior body portion, thereby applying pressure to the patient's soft tissue and forming an open back area between the side portions. Flexible straps are attached to the orthosis body for attaching a lumbar pad to the posterior body portion.

BRIEF DESCRIPTION OF THE DRAWINGS

Other objects, features, and advantages of the present invention will be apparent from the written description and the drawings, in which:

FIG. 4 is a front elevation of the orthosis in accordance with FIGS. 1 through 3;

FIG. 5 is a magnified view of the strap of the orthosis;

FIG. 6 is a perspective view of the stockinette applied to a patient along with measuring tapes;

FIG. 7 is a front elevation of the stockinette on a patient having markings thereon;

FIG. 8 is a perspective view of the patient after casting;

FIG. 9 is a partial perspective view of the cast being removed from the patient;

FIG. 10 is a perspective view of the mold mounted to a mold stand; and

FIG. 11 is a flow diagram of the process in accordance with the present invention.

DESCRIPTION OF THE PREFERRED EMBODIMENT

Figure 2:
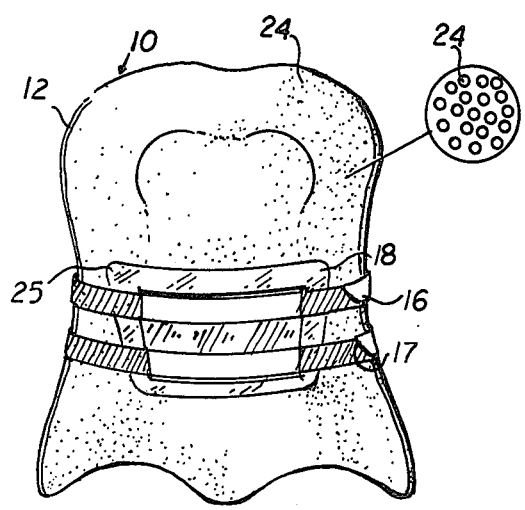
FIG. 2 is a rear elevation.
Figure 1:
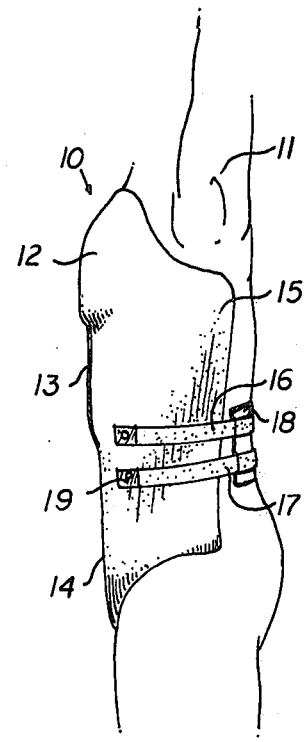
FIG. 1 is a side elevation of an orthosis in accordance with the present invention attached to a patient.
Figure 3:
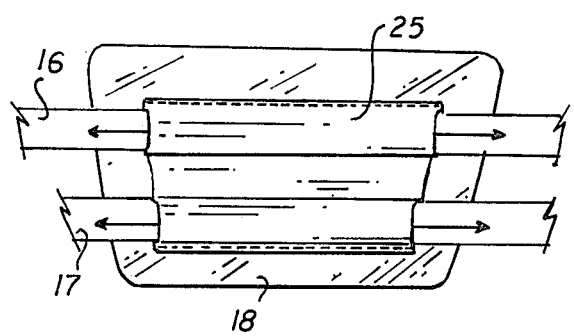
FIG. 3 is a rear elevation of the lumbar pad.

Referring to the drawings, and especially to FIGS. 1 through 5, an anterior total contact hyperextension orthosis apparatus is illustrated in which the support for the orthosis is primarily with the soft tissue of a patient rather than applied to boney areas. The orthosis 10 is shown attached to a patient 11 and has a breast support area 12, an anterior center support area 13, and a pubic support area 14, along with side support areas 15. As seen in these figures, the orthosis 10 is formed to fit the patient and to be supported against soft tissue, and as will be explained in more detail hereinafter, areas of boney protrusions have been built up on the mold to allow extra space and padding to prevent irritation of these areas. The orthosis 10 has a pair of flexible straps 16 and 17 attached to the body thereof on one side with rivets 19, or the like, and passing through a lumbar pad 18 for supporting the lumbar pad and then through a pair of buckles 20 attached with rivets 21 to the body of the orthosis 10. The straps 16 and 17 have hook and loop material having hooks 22 and loops 23 mounted adjacent each other on a strap so that the strap can be pulled through the buckle 20 and wrapped around to engage the hook and loop material 22 and 23 together, so that the straps can be easily and quickly adjusted and the orthosis can be rapidly attached to the patient. The main body of the orthosis 10 is made of a low density polyethylene lined on the inside with a foam rubber material, such as pelite, having a synthetic cloth on one side with small air openings, as illustrated by 24 in FIG. 2. The straps 16 and 17 pass through strap supports 25 attached to a standard lumbar pad 18, which may be lined with a smooth flexible vinyl supporting a resilient pad against a rigid frame member. The orthosis as illustrated is made for the individual patient to apply pressure uniformly over the soft tissue of the anterior portion of the patient's trunk, rather than specifically applying pressure to the sternum and the pubic area in a typical hyperextension orthosis. To accomplish this result requires modification to a standard casting of the patient's body in that the patient lying in the supine position tends to have the breast shift to one side and flatten out, thereby giving an improper position and size so that the casting and mold may differ from, and will not be supported by, the soft tissue of the breast. Similarly, the patient and mold are marked so that the iliac crest and the edge of the rib cage area can be built up to prevent the boney protrusions in these areas from supporting the brace and being irritated by the brace. The mold is built up so that the brace itself has a slightly enlarged area in these portions of the patient's body and the enlarged portions then have additional built up foam lining mounted therein, thereby allowing greater comfort while supporting the brace on the soft tissue of the patient.

The method of making a hyperextension orthosis in accordance with the present invention is illustrated in FIGS. 6 through 11. In FIG. 6 a stockinette 26 has been applied to the patient 27 and measuring tapes 29 are used to measure the breast area, the waist area and the area around the pelvis. The stockinette is then marked with a transferable dye, as seen in FIG. 7, with the breast area marked at 28, the rib cage area 30, and the iliac crest 31, marked on the stockinette 26. In FIG. 8 a cast 32 is formed on the stockinette using a plaster, much in the manner of forming a cast for a broken bone. Once the cast 32 is dry, it is removed, as seen in FIG. 9, using a pair of surgical snips 33 to cut the back of the stockinette 26 to remove the stockinette and the cast 32. The casting is then cleaned up and has the dye marks 28, 30, and 31 transferred to and formed in the interior of the casting 32. The casting is then used to form a drape mold 34, formed of a foamed polymer which then conforms to the patient's body except for the breast area, and has the dye markings thereon which have transferred from the casting. The mold is then mounted to a mold stand 35 and has a pair of breast cups 36 sized for the particular patient pinned with pins 37 to the mold 34 in the position marked by the dye 28, which has been transferred to the mold. Thus, the mold has the breast portion for the particular patient positioned in the proper position and in the proper size to precisely fit the patient with an orthosis formed on the mold for the soft tissue of the breast to support the breast support portion of the orthosis. In addition, the iliac crest portion marked with the dye at 31 is built up as shown at 38, while the edge of the rib cage as marked with the dye at 30 in FIG. 7, is built up as shown at 40. Thus, when the orthosis is drape formed on the mold, an enlarged area will appear at 40 and 38 which can then be filled with foam lining to relieve any pressure against the protruding bones in these areas. This assures that the orthosis is supported primarily by soft tissue, without putting undue pressure on the iliac crests, sternum or rib cage. Once the mold 34 is completed and trimmed, a foam rubber liner, such as pelite, is draped over the mold, and a heated sheet of low density polyethylene is heated and draped over the mold where the liner adheres to the sheet of polymer to form an orthosis complete with liner. The orthosis portion is removed and trimmed to smooth out the edges and may have additional foam added at pre-determined portions if desired, at which time the straps 16 and 17 are attached thereto such as with rivets, along with a lumbar pad 18 and the buckles 20, as illustrated in FIGS. 1 through 5.

It should also be clear that the mold 34 is checked for final dimensions in accordance with the patient's measurements prior to making the orthosis, as shown in FIG. 6, to assure that proper sizing has been accomplished. FIG. 11 shows a flow diagram in which the stockinette is applied to the patient and pre-determined markings are made at 28, 30, and 31, and at which time the measurements are taken with the tape 29, then the steps of applying the caster, cast and forming the drape mold in the cast, this step is followed by the mounting on the mold stand and the pinning of the breast cups in the marked positions using breast cups of the appropriate size, and building up the mold portions 38 and 40, drape forming a liner over the mold 34, then drape forming the plastic sheet on the mold, trimming the orthosis, and attaching the straps and lumbar pad.

It should be clear at this point that an anterior total contact hyperextension orthosis has been provided, along with a method of making an orthosis for a particular patient. It will also be clear that the total contact hyperextension orthosis must be individually made for the patient in order to get a uniform spread of pressure against the soft tissue to provide a more comfortable orthosis for the patient, and which can remain fairly cosmetically acceptable under the clothes of the patient. The apparatus and method are, however, not intended to be limited to the particular forms shown, which are to be considered illustrative rather than restrictive.

I claim:

1. A method of making an anterior total contact hyperextension orthosis which utilizes contact with a patient's breasts as a supporting surface comprising the steps of:

placing a stockinette on a patient;
   marking the stockinette with a transferrable dye to mark the position of the patient's breasts;
   measuring the patient's breast for size in a standing or sitting position;
   forming a cast on a patient's body over said stockinette with the patient being in a supine position;
   removing the cast and forming a mold therein having the dye markings thereon transferred from the marking made on said stockinette for said patient's breast position;
   mounting the mold onto a stand;
   modifying the mold to conform to a patient, including mounting breast cup molded parts to conform to the measured patient's breast in a standing or sitting position on the dye marked portion of said mold; and
   drape forming an anterior hyperextension orthosis on the mold formed to apply a uniform support pressure on the patient's breasts.

2. The method in accordance with claim 1, in which the modifying of said mold to conform to a patient includes the enlarging of the iliac crest on the mold.

3. The method in accordance with claim 2, in which the steps of modifying the mold to conform to a patient includes the building up of the edge of the rib cage of the mold.

4. The method in accordance with claim 3, including the step of attaching flexible straps having hook and loop material on one end thereof for attaching through buckles attached to the main body of the orthosis.

5. The method in accordance with claim 4, in which the step of forming an anterior hyperextension orthosis on said mold includes draping a foam polymer lining material over the mold and draping a low density polyethylene heated sheet over the mold, removing the hyperextension orthosis body and trimming prior to attaching the flexible straps thereto.

* * * * *